United States Patent
Segall et al.

(10) Patent No.: US 7,027,145 B2
(45) Date of Patent: Apr. 11, 2006

(54) RECONFIGURABLE SURFACE FINISH INSPECTION APPARATUS FOR CYLINDER BORES AND OTHER SURFACES

(75) Inventors: Stephen B. Segall, Ann Arbor, MI (US); Yoram Koren, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 216 days.

(21) Appl. No.: 10/603,051

(22) Filed: Jun. 24, 2003

(65) Prior Publication Data

US 2004/0263855 A1    Dec. 30, 2004

(51) Int. Cl.
G01N 21/00    (2006.01)

(52) U.S. Cl. .................. 356/241.1; 356/237.2

(58) Field of Classification Search .. 356/241.1–241.6, 356/237.1–237.5, 445–448
See application file for complete search history.

(56) References Cited

U.S. PATENT DOCUMENTS

| | | | | |
|---|---|---|---|---|
| 3,761,186 | A | * | 9/1973 | Wason ...................... 356/241.1 |
| 4,055,382 | A | * | 10/1977 | Ziekman et al. ............ 356/446 |
| 4,268,169 | A | * | 5/1981 | Stenning .................. 356/241.1 |
| 4,334,780 | A | | 6/1982 | Pernick |
| 4,774,751 | A | * | 10/1988 | Pryor ...................... 29/407.04 |
| 4,861,984 | A | * | 8/1989 | West .......................... 250/236 |
| 5,004,339 | A | * | 4/1991 | Pryor et al. .............. 356/241.1 |
| 5,189,490 | A | | 2/1993 | Shetty et al. |
| 5,339,152 | A | * | 8/1994 | Horn .......................... 356/458 |
| 5,517,311 | A | * | 5/1996 | Takeuchi et al. ............ 356/606 |
| 5,757,496 | A | * | 5/1998 | Yamazaki ................... 356/600 |
| 5,793,488 | A | * | 8/1998 | Kulawiec et al. ........... 356/512 |
| 5,940,302 | A | * | 8/1999 | Pryor ........................ 700/195 |
| 6,084,671 | A | | 7/2000 | Holcomb |
| 6,355,495 | B1 | * | 3/2002 | Fujino et al. ................. 438/18 |
| 6,512,578 | B1 | * | 1/2003 | Komatsu et al. ......... 356/237.5 |
| 6,567,162 | B1 | | 5/2003 | Koren et al. |
| 2003/0218741 | A1 | * | 11/2003 | Guetta ..................... 356/237.1 |

OTHER PUBLICATIONS

G.J. Dixon; Light Scattering Maps Surface Imperfections; Optical Engineering: Surface Scattering; Laser Focus World; www.optoelectronics-world.com; Nov. 1998; pp. 89-94.

SMS; A New Light on Quality; Interpreting Light Scatter Measurements; Schmitt Measurement Systems, Inc.; Apr. 1994; pp. 1-19.

(Continued)

*Primary Examiner*—Michael P. Stafira
(74) *Attorney, Agent, or Firm*—Harness, Dickey & Pierce, P.L.C.

(57) ABSTRACT

A reconfigurable inspection apparatus for inspecting a surface finish of a cylinder bore or other machined surface. The apparatus may include a reconfigurable multi-spindle apparatus supporting a plurality of inspection probes. Each probe may include a laser that directs a laser beam perpendicularly to the machined surface, and a detector positioned at an angle to the laser beam to detect scattered laser light from the surface. The probe may also include a computer system including software that compares the detected scattered light to a scattered light signature from a first-type finishing mark and to a scattered light signature from a second-type finishing mark and determines a condition of the surface finish.

28 Claims, 7 Drawing Sheets

OTHER PUBLICATIONS

Thomas A. Germer et al.; Polarized Light Scattering Measurements of Polished and Etched Steel Surfaces; Scattering and Surface Roughness III, Z.-H Gu, and A.A. Maradudin, Eds., Proc. SPIE 4100, 148-155 (2000).

Cz. Lukianowicz, et al.; Optical System for Measurement of Surface Form and Roughness; Measurement Science Review, vol. 1, No. 1, 2001; pp. 151-154.

* cited by examiner

RECONFIGURABLE SURFACE FINISH INSPECTION APPARATUS FOR CYLINDER BORES AND OTHER SURFACES

FEDERALLY SPONSORED RESEARCH

Certain of the research leading to the present invention was sponsored by the United States Government under National Science Foundation Grant No. EEC-959125. The United States Government has certain rights in the invention.

BACKGROUND OF THE INVENTION

Many high-precision machined parts are produced in a multi-step process. First the surface is machined, possibly from a casting, to give it the approximate desired dimensions. Then the surface is honed, ground or cut in a finishing operation that removes only a very thin layer of metal to produce the desired precise dimensions and surface finish. Examples of this multi-step process are the face milling of flat surfaces in engine heads and engine blocks and the machining of cylinders in engine blocks. The cutting tools used to perform these operations must be precisely located and aligned. This is particularly important for the finishing tools, because they remove a very thin layer. If they are not properly positioned, they may miss the metal surface entirely in some places leaving only a coarser finish in those places.

A specific case of multi-step machining is the machining of cylinder bores. In the machining process the cylinders of an engine are first machined in one or more boring operations, usually a coarse and fine boring operation. Then the cylinders are finished by going through one or more honing operations until the final finish is achieved. If the machining marks from the boring operation have not been removed in the honing operation, the cylinder may burn oil and generate noise when the engine is running.

In a cylinder bore, if the coarse and fine tools are aligned in the same direction but are not perfectly concentric, a strip along the inside surface of the cylinder could remain coarsely finished after the fine finishing process. If tools are centered on the axis of the cylinder, but are not at precisely the same angle of inclination, a strip of coarse bored surface may extend part of the way down one side of the cylinder and continue on the opposite side of the cylinder along the rest of its length. By mapping the pattern of coarse and fine finished regions it may be possible to determine the type of misalignment that caused the problem so that it could be quickly corrected without producing additional defective parts.

Differences in surface finish can be recognized by inspection by a knowledgeable expert, but human inspection is not totally reliable. An automated inspection procedure for inspecting surface finish for cylinder bores that is faster, less subjective and more reliable than human inspection is desirable. It is also desirable to automatically distinguish between surfaces with different finishes to determine whether the machining operations have been performed as intended.

The use of scattered light to obtain information about surface structure has been studied extensively. A summary of different measurement techniques is given in an article by G. J. Dixon entitled "Light scattering maps surface imperfections" *Laser Focus World* pages 89–94, November 1998. Much of the work in this area is directed at obtaining detailed surface profiles or values of surface roughness from scattering measurements. These techniques are capable of distinguishing between different surface finishes, but they are not designed to obtain this information sufficiently rapidly over large areas of machined metal surfaces to be used for one hundred percent in-process inspection.

Another technique that is used to infer surface roughness is total integrated scattering. The theory to evaluate these measurements is only valid when the surface roughness is small compared to the wavelength of the probing light, which is not the case in machining processes. Optical Dimensions of Bozeman, Mont. has developed a device to measure surface roughness using scattered light, but it can only provide repeatable values independent of the direction of incidence when the scattering is independent of the orientation of the surface being measured. This will be the case for ground surfaces, not surfaces with a pattern of machining marks. When machining marks or honing scratches are present, light is preferentially scattered in planes perpendicular to these machining marks. Angle resolved scattering techniques have been developed to analyze the scattering patterns produced by these surfaces. Analysis of this data is generally a lengthy, time consuming process that is usually performed only in research labs.

A cost effective apparatus that is capable of inspecting large surface areas rapidly in real time manufacturing processes is desirable.

SUMMARY

One embodiment of the invention provides a reconfigurable inspection apparatus for inspecting a surface finish of a cylinder bore or other machined surface. The inspection apparatus may include a reconfigurable multi-spindle apparatus supporting a plurality of inspection probes. Each probe may include a laser that directs a laser beam perpendicularly to the machined surface, and a detector positioned at an angle to the laser beam to detect scattered laser light from the machined surface. The probe may also include a computer system including software that compares the detected scattered light to a scattered light signature from a first-type finishing mark and to a scattered light signature from a second-type finishing mark and determines a condition of the surface finish.

BRIEF DESCRIPTION OF THE DRAWINGS

In the accompanying Figures, there are shown present embodiments of the invention wherein.

DETAILED DESCRIPTION OF THE INVENTION

Figure 1:
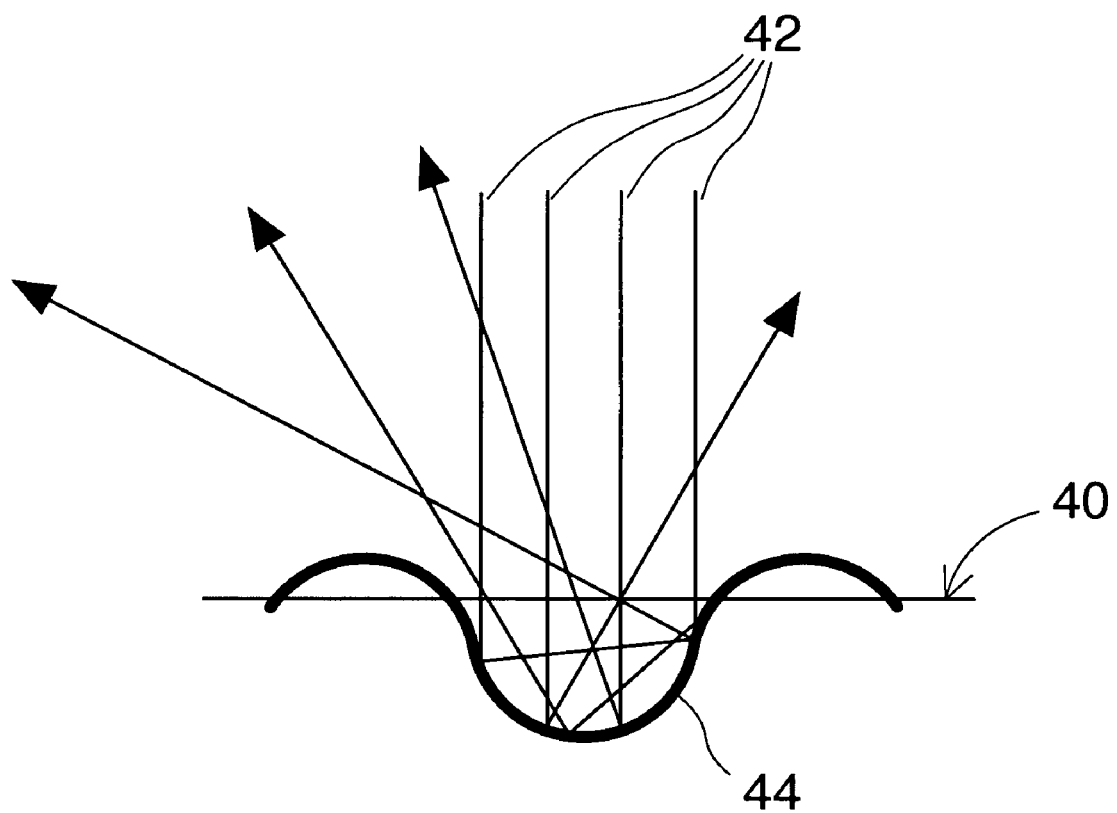
FIG. 1 is a schematic view showing scattering of laser light from grooves produced by a cutting tool.

Referring now to the drawings for the purpose of illustrating the invention and not for the purpose of limiting the same, it is to be understood that standard components or features that are within the purview of an artisan of ordinary skill and do not contribute to the understanding of the various embodiments of the invention are omitted from the drawings to enhance clarity. In addition, it will be appreciated that the characterizations of various components and orientations described herein as being "vertical" or "horizontal", "right" or "left", "side", "top" or "bottom", are relative characterizations only based upon the particular position or orientation of a given component for a particular application.

Before proceeding with the detailed description of the various embodiments of the present invention, angle dependent scattering as applied to such embodiments is described.

Manufactured parts or products typically include surfaces that have been subjected to operations such as cutting, honing, grinding, milling, etc, all of which may leave marks on the machined surfaces. In a face milling or boring operation, for example, the tool scrapes a chip off the surface of the material. As the edge of the tool moves across the surface it leaves microscopic grooves in the surface. These are referred to as machining marks. The pattern left by the cutting tool can be observed with the naked eye.

When a surface 40 is bored or surface-milled, light 42 incident perpendicularly to the surface 40 will not be scattered equally in all directions. See FIG. 1. Instead, the incident light 42 will be strongly scattered in directions perpendicular to the machining markings on the machined surface with less scattering in other directions. The reason is that the metal surface reflects most of the light, but the microscopic surface variation produced by the cutting tool causes the reflected rays to emerge in many different directions. Much of this variation is due to a pattern of grooves 44 on the metal surface. These grooves 44 reflect light perpendicular to the length of the grooves 44, but reflect very little light along the direction of the grooves 44. If the machining marks are all in one direction, the direction of the scattered light will be well defined in a narrow sheet. If the pattern is cross hatched or contains more than one direction of marks the scattering will be distributed in a number of directions with multiple or broad intensity peaks. In a production line continually producing the same part, each part is made using identical machining operations. Therefore, the pattern of machining marks is known and scattering produced by a particular pattern should be the same from piece to piece. By mapping the intensity pattern of scattered light as a function of angle around the incident beam direction, angular locations can be found for which the scattering for a particular surface finish is significantly different than that for another finish. In embodiments of the present invention, by measuring scattering at particular angles, it is possible to distinguish between surfaces with different surface finishes.

Extensive studies have been performed on the scattering of light from manufactured surfaces. These studies and associated measurement techniques can measure scattered light as a function of angle and intensity and have been done to obtain surface profiles and surface roughness values. Raster scans that scan a scattering signal for a particular angle of incidence and angle of detection over an entire surface can obtain a scattering profile of the surface for that angle of incidence and detection. The present invention is a type of raster scan that is used for a particular application—comparing scattering from the same part surface before and after one or more machining operations have been performed on the surface in order to determine whether the operations have been performed over the entire desired surface area. The purpose of this measurement is not to obtain detailed information about surface profile or surface roughness, but simply to rapidly verify that a desired manufacturing operation has been carried out over the desired area. To obtain this information rapidly we design the measurement probe to look for a particular scattering signature. A scattering signature is a feature of the scattered light pattern that exists for one surface and is absent or greatly diminished for the second surface. For example, one surface may have a peak signal at a particular angle relative to the part surface, whereas the second surface may lack that feature. By looking specifically for a feature that differentiates one surface from another, we can rapidly determine whether the manufacturing operation that replaced one surface with another was performed over the entire desired surface area.

For the example of a machined surface, the desired scattering signature could be inferred from the pattern of machining marks produced on the surface. The existence of the signature could also be confirmed experimentally using standard measurement techniques for determining scattering intensity as a function of angular position around a beam. This could be done for known surface finishes before and after one or more machining operations.

Figure 2:
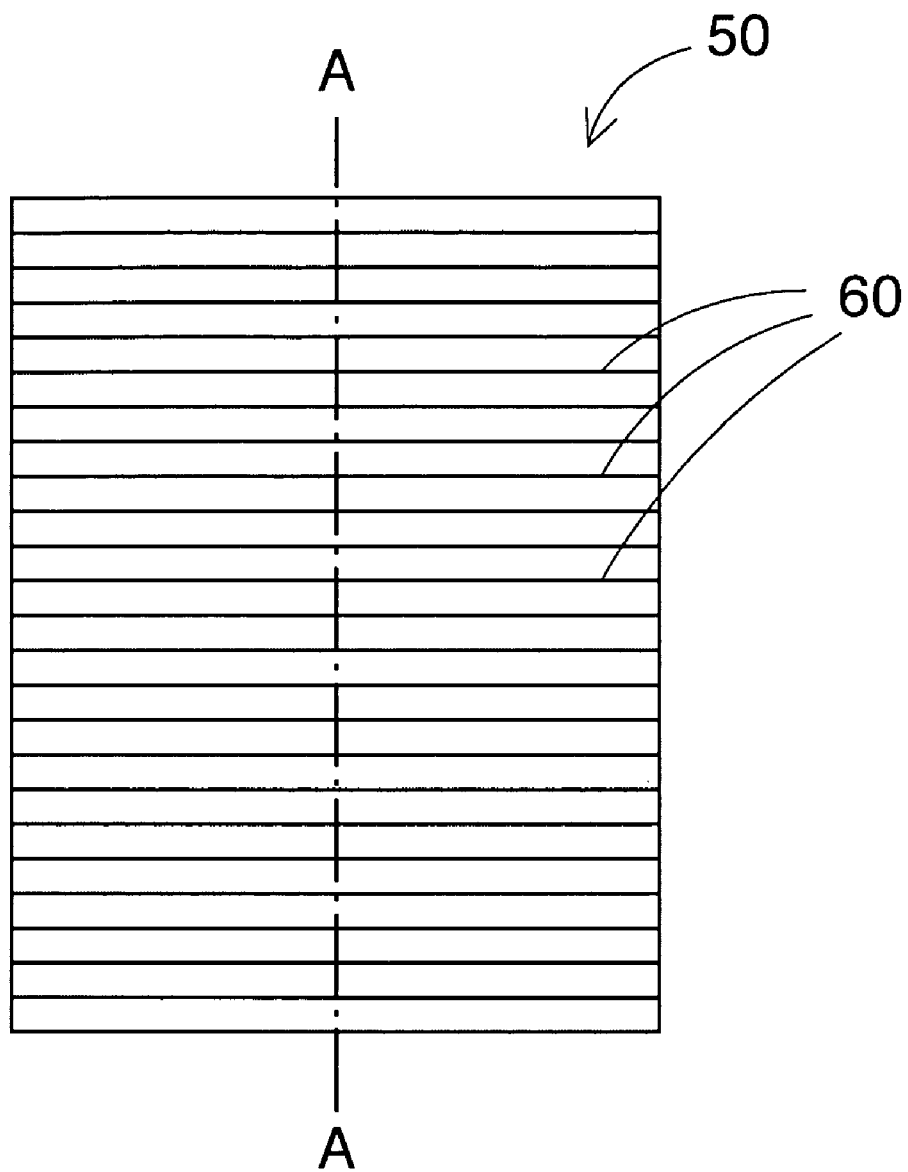
FIG. 2. is a schematic view showing marks produced in a cylinder by a boring operation.

A cylinder 50 is machined in one or more boring operations followed by honing operations. Boring produces a series of machining marks 60 ("boring marks") that are essentially perpendicular to a longitudinal axis A—A of the cylinder 50. See FIG. 2. These unidirectional marks 60 produce a scattering pattern in a well defined plane perpendicular to the direction of the markings.

Figure 3:
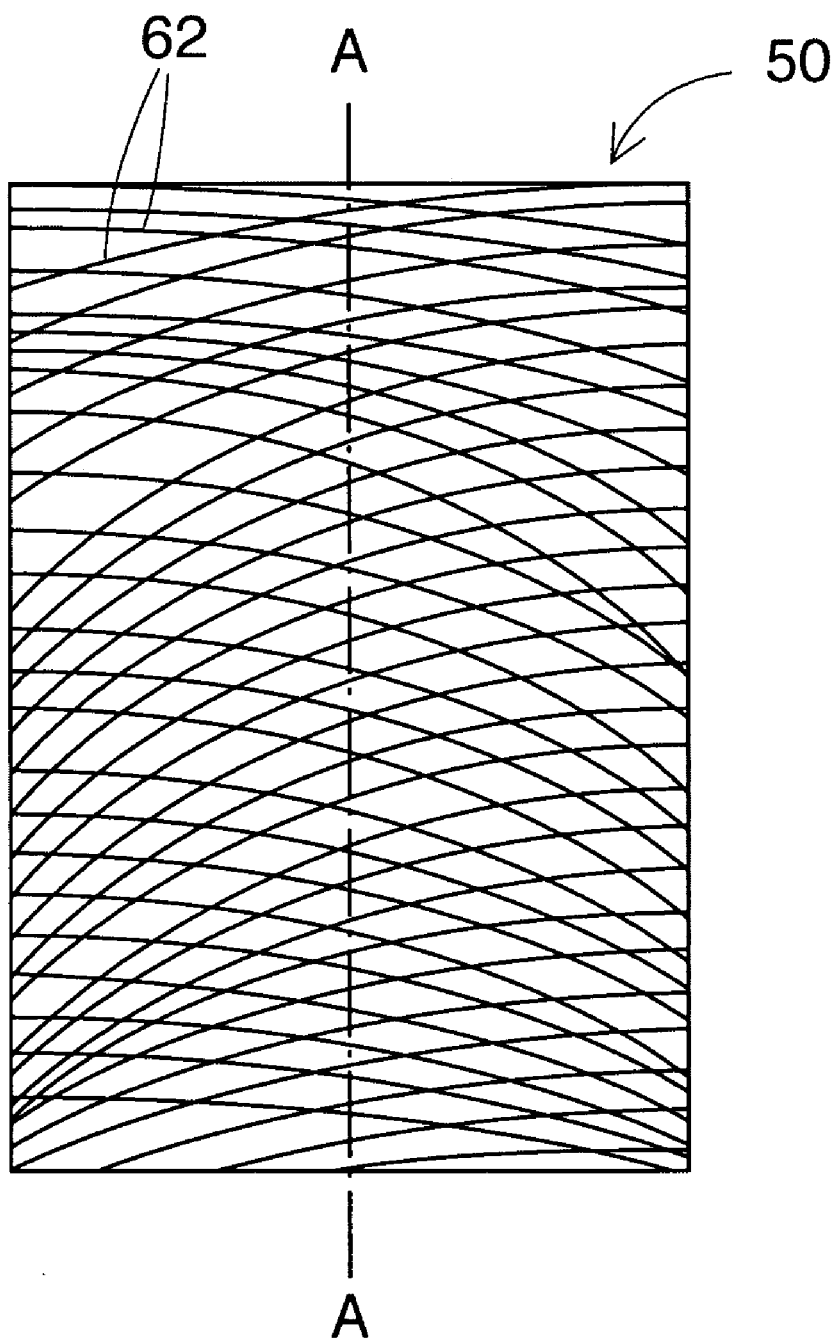
FIG. 3 is a schematic view of marks produced by a honing operation.

Honing is performed by moving a set of grinding stones up and down inside the cylinder 50 as the stones are rotating. This produces a cross hatched pattern of scratch marks or honing marks 62, as shown in FIG. 3. As the honing tool moves up and down, its axial velocity oscillates from zero at the top and bottom of the stroke to a maximum velocity in the middle of the stroke. This produces an array of honing marks 62 that vary in direction from honing marks 62 that are perpendicular to the axis A—A of the cylinder 50 up to some maximum angle determined by the rotation rate and the maximum axial velocity of the honing tool.

Figure 4:
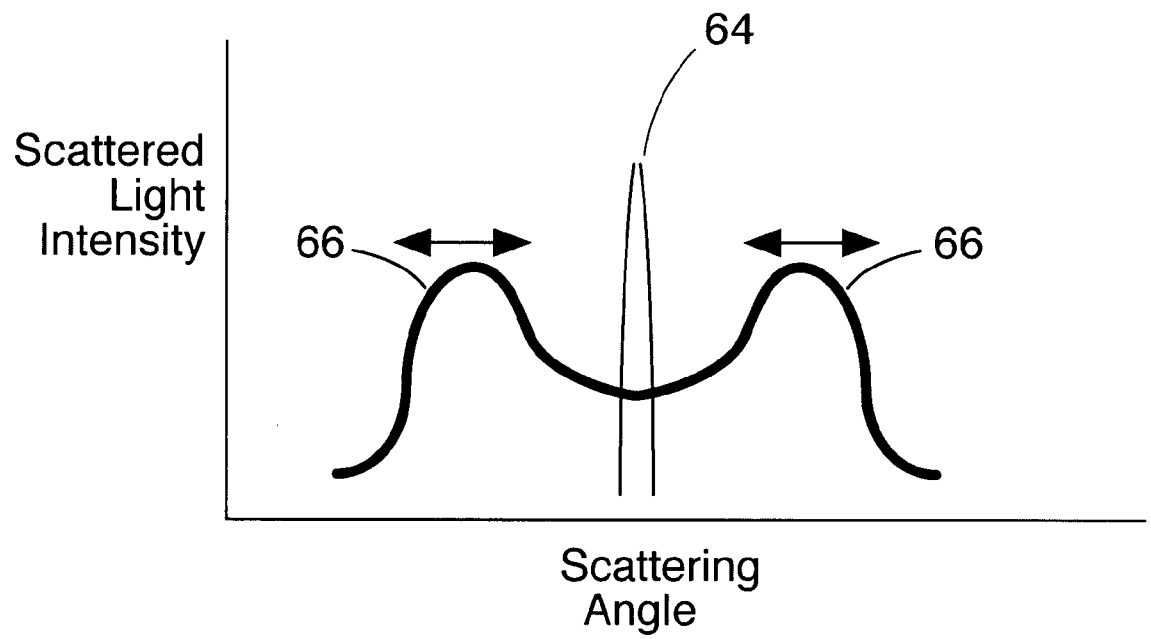
FIG. 4 is a schematic graph showing scattered light intensity around an incident beam as a function of angle from boring and honing marks.

The honing marks 62 produce scattering over a range of angles. The scattering is in planes perpendicular to the honing marks 62 and covers the range of angles defined by the honing marks 62. A graph showing a comparison of the scattering pattern expected from boring marks 60 with the scattering pattern expected from the honing marks 62 inside the cylinder 50 is shown in FIG. 4. The graph covers only 180° of scattering angle, as the remaining 180° produces a symmetric signature pattern. In the following discussion, only one half of the symmetric scattered light signature is described.

Figure 5:
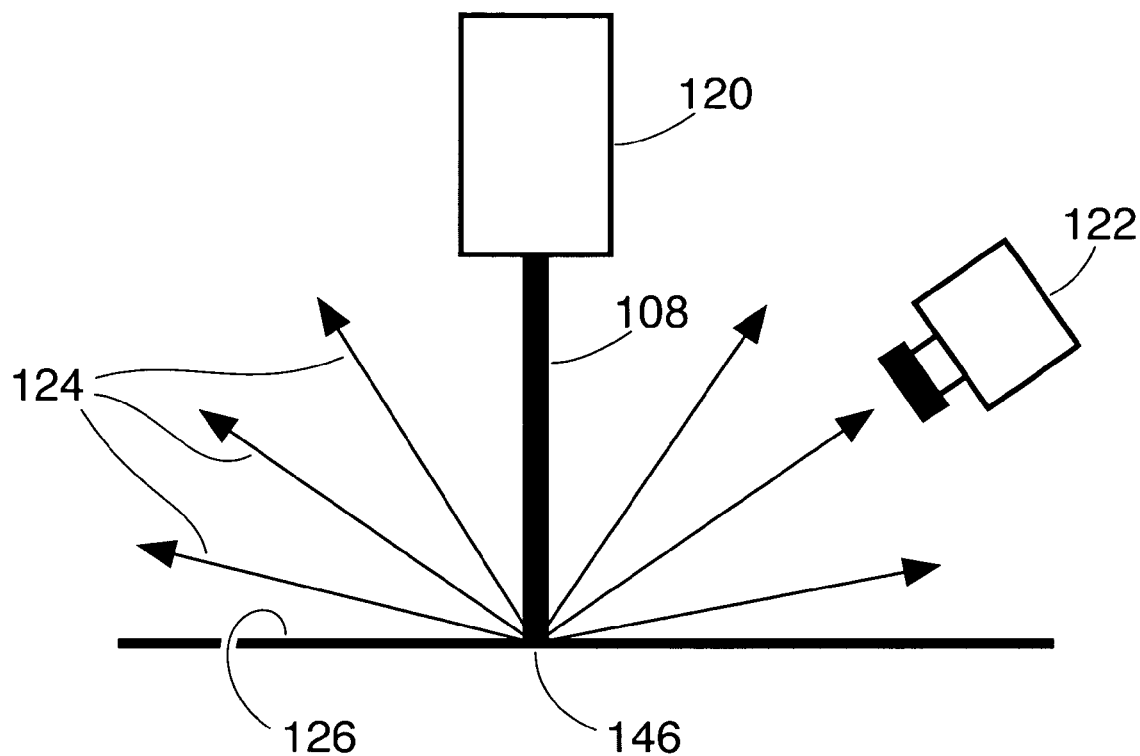
FIG. 5 is a schematic view showing light scattered by a surface being inspected according to an embodiment of the present invention.

As shown in FIG. 4, the scattered light from the boring operation is preferentially scattered in a narrow plane along the axis A—A of the cylinder 50 producing a (half) signature with a single narrow peak 64, while the honing operation produces a (half) signature with two broad peaks 66 on either side of this plane. The location of the peaks 66 can vary, because the range of axial velocities of the honing tool is different at different axial locations in the cylinder 50. If a laser beam 108 is directed perpendicularly to a surface 126 of the cylinder 50, and a photo detector 122 is placed on the axis A—A of the cylinder 50 pointed towards a spot 146 produced by the laser beam 108 on the surface 126, the photo detector 122 will be in the plane of preferential scattering from a bored surface. See FIGS. 5 and 6. If the honing operation has not removed the machine markings from the boring operation, the signal observed by the detector 122 will be significantly larger than if the boring marks 60 were absent. If the boring marks 60 are not present, there will still be scattered light reaching the detector 122 from the honing marks 62, but these signals will have lower intensity. Comparison of a cylinder with an acceptable surface finish, i.e., only honing marks 62 producing scattering, with a defective cylinder in which the scattered light signature from boring 60 is still observable will show a greater scattering signal when the boring marks 60 have not been removed. This difference may be used to distinguish between acceptable and defective cylinder surface finishes, when the detector 122 is a single diode. Comparison of the scattered light signature with the signatures from both boring marks 60 and honing marks 62 may be performed when the detector 122 is of the line scan type. It would be appreciated that instead of boring marks 60 and honing marks 62, other types of surface marks that are produced during manufacturing of a part and have different degrees of coarseness may be distinguished by their characteristic scattered light signatures.

This measurement is different than a profilometry measurement in which the actual profile of the surface is measured. As applied to the present invention, the measurement does not obtain detailed information about surface profiles or surface roughness from scattering data, but only uses the information from angle resolved scattering measurements that is necessary to distinguish between surface finishes. It does not measure surface roughness, but only determines the presence or absence of a particular scattering signature. An inspection procedure may establish a threshold signal above which that segment of the surface being inspected would not have been sufficiently machined by the honing operation.

Figure 6:
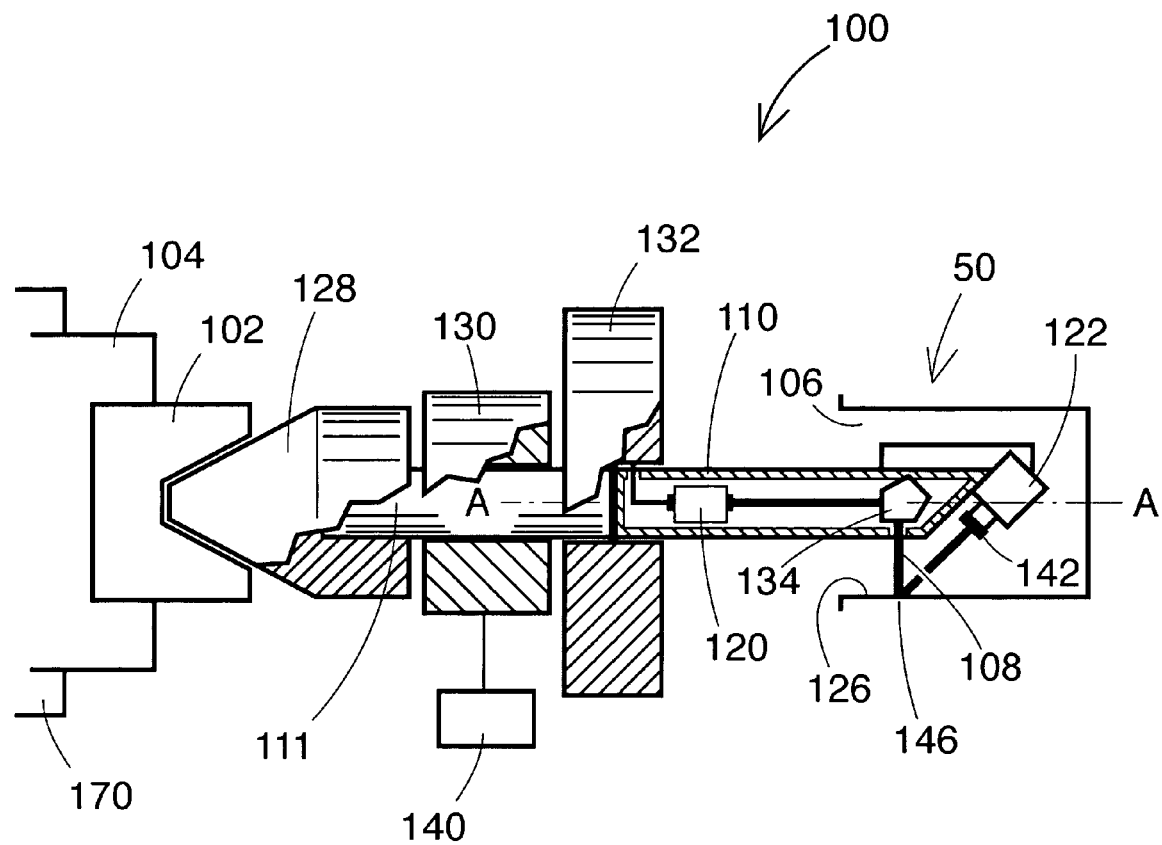
FIG. 6 is a schematic view of an embodiment of a surface finish inspection probe according to the present invention.

An embodiment of a surface-finish inspection probe 100 that may be used to inspect a surface finish, such as, for example, the finish of the surface 126 of a cylinder bore 106, by employing angle dependent scattering to distinguish between types of surface finishes, is shown schematically in FIG. 6. The inspection probe 100 may include a diode laser 120 mounted inside a tube 110. The tube may be mounted on a support shaft 111, which is mounted on tool holder 128. The inspection probe 100 may include an optical device 134, such as a pentaprism, to reflect the laser light perpendicularly to the axis A—A. The tool holder 128 may be inserted into a spindle 102 of an inspection machine 104 and the inspection probe 100 may be inserted into a cylinder bore 106. In the cylinder bore 106 light from the laser 120 is incident perpendicular to the surface 126 of the cylinder 50. If the surface 126 of the bore 106 were reflective, the laser beam 108 would be reflected back on itself and no light from the beam would be detected by the photo detector 122. See FIG. 5. If light is detected outside the region of the incident beam 108, this light would have been scattered, rather than reflected, from the machined surface 126 of the part. The scattered light 124 may be observed by measuring the light leaving the surface 126 at an angle relative to the incident beam 108.

The detector 122 may be positioned to measure light scattered from the incident beam 108 of the laser 120 at an angle with the axis A—A of the cylinder 50, such that the detector 122 is directed toward the spot 146 produced by the laser beam 108 on the machined surface 126. The detector 122 may be a single photo diode, an array of photo diodes or a line scan detector. These detectors 122 are commercially available and may include photo diodes that incorporate their own amplifiers. Single photo diodes and diode arrays may be obtained, for example, from UDT Sensors Inc., Hawthorne, Calif.

The inspection probe 100 may be rotated as it is inserted into the cylinder 50, so that a map of the scattered light intensity from the entire inside surface 126 of the cylinder 50 can be obtained. An optical filter 142 may be placed in front of the detector 122 to filter out signals from ambient light or other than directly scattered laser light that might inadvertently enter the detector 122. The filter 142 may reduce the signal to noise ratio for the detector 122. Suitable commercial filters 142 are available, for example, from Edmund Industrial Optics, New Jersey.

The inspection probe 100 may include a power device 130 transmitting electric power to the laser 120 and to a detector electronics device 132, and transmitting the signal from the detector 122 to a computer system 140 that includes data acquisition and signal processing software. In one embodiment, the power device 130 may be a slip ring, i.e., a donut-shaped device mounted on the support shaft 111, as shown in FIG. 6. The detector electronics device 132 may also be in the form of a donut-shaped canister mounted on the support shaft 111. The detector electronics device 132 may amplify, filter or otherwise process the detected signals.

Signals from the detector 122 may be sent to the computer system 140. The signals are processed in the computer system 140 using commercially available data reduction software, such as MATLAB®, from MathWorks, Natick, Mass. The results may be graphically displayed using a 3D graphical software, such as MATLAB®, or software supplied by other commercial vendors. The data may be color-coded for convenience. Inspected cylinders 50 or cylinder blocks can be designated as acceptable or defective based on the corresponding signatures as described above, i.e. signatures exhibiting high boring peaks 64 indicate defective cylinders. Detailed maps of scattering from the entire surface of each cylinder bore 106 could be viewed, if desired.

Although in the context of cylinder bores 106, the machined surfaces 126 are metallic, the inspection probe 100 is not limited to inspecting only such surfaces. Any surface that would be reflective if highly polished and has been subjected to a manufacturing process that produces a scattered light signature may be inspected, such as, for example, ceramic surfaces with glass-like finish, wood surfaces with polished coating, etc. Surfaces that are flat rather than curved could be also inspected using the inspection probe 100.

Figure 7:
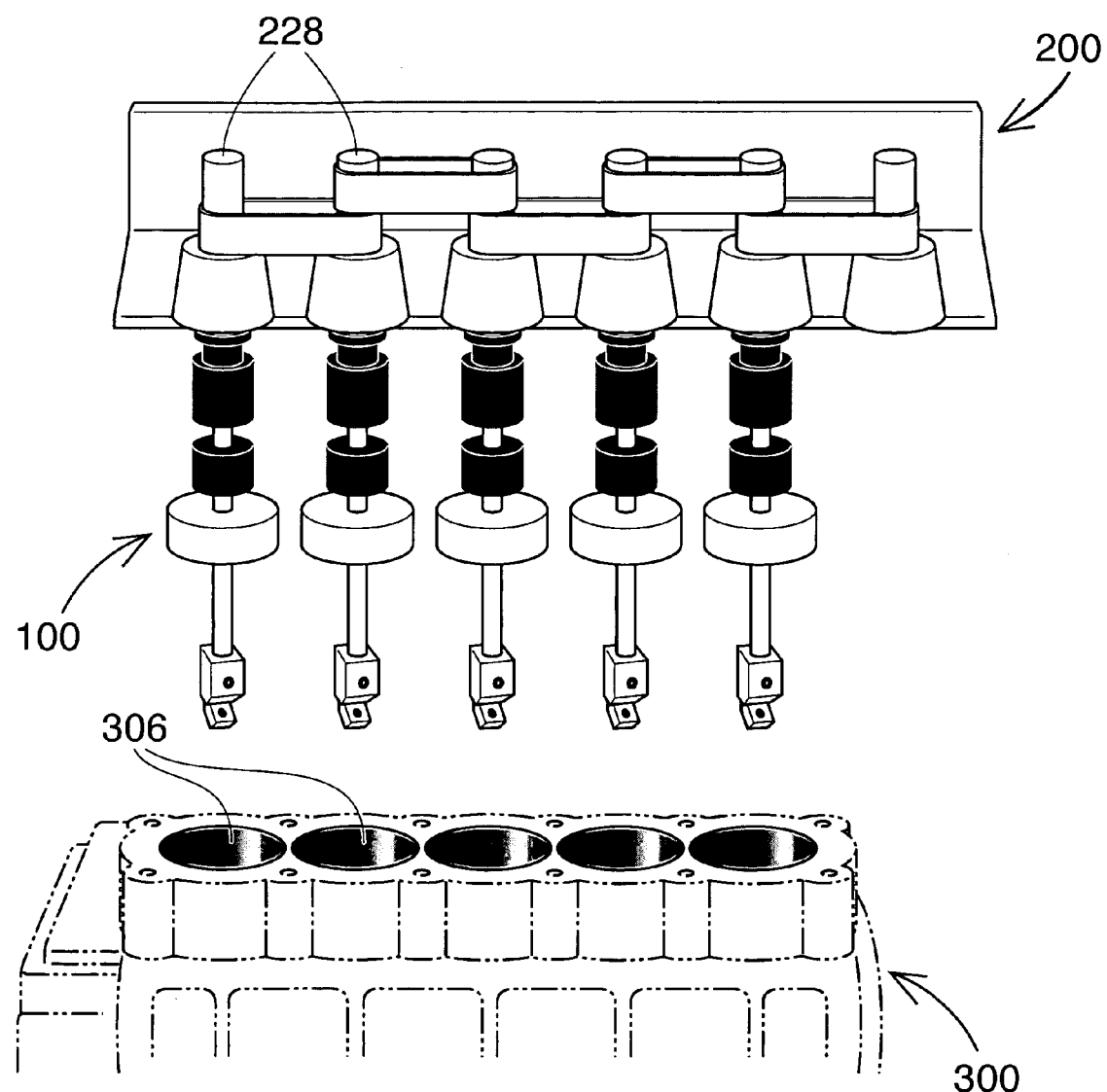
FIG. 7 is a schematic view of a reconfigurable surface finish inspection system according to the present invention.

The inspection probe may be used with a CNC machine 170 programmed to inspect the cylinders of an engine block sequentially or a multi-spindle machine dedicated to inspection of a particular engine block. See FIGS. 6 and 7. In one embodiment, one or more inspection probes 100 may be reconfigurably mounted in a reconfigurable multi-spindle apparatus 200, such as the one described in U.S. Pat. No. 6,569,071, co-owned by the assignee, The Regents of the University of Michigan. The multi-spindle apparatus 200, which is shown schematically in FIG. 7, has a plurality of inspection probes 100 that are simultaneously inserted into corresponding bores 306 of a multi-cylinder engine block 300, for example, or into machined bores of other products or parts. The multi-spindle apparatus 200 is reconfigurable, wherein, as defined here, reconfigurable includes changing the number of spindles 228, changing the relative position of the spindles 228 in relation to the multi-spindle apparatus 200, and changing the distance between any two spindles 228. Changing the distance between any two spindles 228 may be accomplished without removing the spindles 228 from the multi-spindle apparatus 200 to inspect different parts of the same part family or of different part families in a real-time manufacturing process, as described in U.S. Pat. No. 6,569,071, the entire contents of which are incorporated herein by reference. Accordingly and in the same sense, a number of inspection probes 100 may be reconfigurably positioned on the multi-spindle apparatus 200, such that the distance between any two probes 100 can be changed during in-process inspection.

For cylinders 50 with different diameters, the distance between the center of the tube 110 and the surface 126 of the cylinder 50 would be different. The inspection probe 100 may be designed so that the location or angle at which the detector 122 is mounted may be adjusted, to accommodate these changes. Alternatively, different inspection probes 100 could be made for different cylinder diameters.

While the example of an inspection probe 100 has been described for the inspection of the inside surface 126 of cylinder bores 106, it would be appreciated that the inspection probe 100 may also be used for flat surfaces in any application in which it is desired to distinguish rapidly and/or in real time in-line process between surface finishes with different machining patterns using angle-dependent scattering. The inspection probe 100 could be used for any manufacturing operation in which material is either added or removed from a surface provided that a scattering signature exists that can distinguish the surface finish before and after removal or addition of material. Examples of operations that may add material include coating, painting, deposition, etc. Examples of operations that remove material include milling, turning, grinding, etc.

Although a large number of different types of profilometers and surface roughness measurement devices have been developed and some of these may be able to easily differentiate between the types of surface finishes considered herein, the inspection probe 100 of the present invention is particularly simple and adaptable to rapid inspection of cylinder surfaces in a production environment. When mounted on a reconfigurable multi-spindle apparatus 200, a plurality of the inspection probes 100 may be configured to inspect parts within the same family of parts, such as, engine blocks with the same pattern of cylinder bores but with different dimensions, or across families of parts, such as engine blocks with different number of cylinder bores.

It should be appreciated that the inspection probe 100 is not a profilometer or surface roughness measurement device, although it may be able to provide some information about these parameters. Instead, the inspection probe 100 measures the scattering signature from a surface that has been machined in a known way. Observation of this signature or its absence makes it possible to distinguish between different surface finishes.

In its various embodiments, the inspection probe 100 can be used to rapidly determine whether a surface has been properly machined to the desired surface finish. One or more inspection probes 100 can be incorporated into a reconfigurable multi-spindle or other reconfigurable inspection machine to rapidly determine whether multiple surfaces have been properly finished on a complex part, such as the cylinders of an engine block. The inspection probe makes specific use of the repetitive grooves that are produced on a microscopic scale on a machined surface to determine whether a surface has been machined to the desired finish over the entire surface. It may determine whether, in a multi-step machining process, the entire surface has been machined to the desired surface finish.

In one embodiment of the inspection probe 100, the light is incident at normal incidence and the scattering is observed at angles at which there will be no reflected light. The inspection probe 100 is advantageously and compactly designed such that the surface being inspected may be rapidly scanned. The compact design places the detector 122 close to the location of the incident beam 108, making it possible to inspect cylinders 50 which can only be accessed from one end.

While particular embodiments of the invention have been described for the purpose of illustrating the invention, it will be appreciated by those of ordinary skill in the art that numerous variations of the details, materials and arrangement of parts may be made within the principle and scope of the invention without departing from the spirit of the invention. The preceding description, therefore, is not meant to limit the scope of the invention, which is to be determined only by the appended claims and their equivalents.

What is claimed is:

1. An inspection probe for inspecting a surface finish of a machined surface, the probe comprising:
   a laser directing a laser beam perpendicularly to the machined surface;
   an optical detector positioned at an angle to the laser beam to detect scattered laser light from the surface; and
   a computer system including software that compares the detected scattered light to a scattered light signature from a first-type finishing mark and to a scattered light signature from a second-type finishing mark and determines a condition of the surface finish, wherein the machined surface is a cylinder bore for an engine block.

2. The probe of claim 1, wherein the optical detector is a photodiode or photodiode array.

3. The probe of claim 1, wherein the optical detector is a line-scan detector.

4. The probe of claim 1, wherein the first-type finishing mark is coarser than the second-type finishing mark.

5. The probe of claim 1, further comprising an optical device for directing the laser beam from the laser perpendicularly to the machined surface.

6. The probe of claim 5, wherein the optical device is a pentaprism.

7. The probe of claim 5, wherein the laser and the optical device are supported inside a tube.

8. The probe of claim 7, wherein the tube is mounted on a support shaft.

9. The probe of claim 8, further comprising a power device transmitting power to the laser and the detector and transmitting data to a computer, the power device being mounted on the support shaft.

10. The probe of claim 9, further comprising a detector electronics device mounted on the support shaft.

11. The probe of claim 10, wherein the shaft is rotatably supported on a tool holder.

12. The probe of claim 11, wherein the tool holder is supported on a spindle.

13. The probe of claim 11, wherein the spindle is supported on a CNC machine.

14. The probe of claim 13, wherein the CNC machine is programmed to sequentially inspect the cylinders of an engine block.

15. The probe of claim 13, wherein the spindle is supported on a multi-probe inspection machine.

16. The probe of claim 15, wherein the inspection machine is a reconfigurable inspection machine.

17. The probe of claim 1, further comprising a filter in front of the detector to reduce unwanted light.

18. The probe of claim 1, wherein each scattered light signature is distinguished by characteristic peaks of scattered light.

19. The probe of claim 10, wherein the detector electronics device include signal amplification.

20. The probe of claim 1, where the machined surface is metallic.

21. A method for inspecting the surface finish of a machined surface, the method comprising:
   directing a laser beam perpendicularly to the machined surface;
   detecting a scattered laser beam light from the machined surface;
   determining a signature of the detected scattered laser beam light; and
   determining a condition of the machined surface from the signature.
   wherein the machined surface is a cylinder bore and, wherein determining a signature includes comparing a scattered light signature from a first-type finishing mark to a scattered light signature from a second-type finishing mark.

22. The method of claim 21, wherein determining a signature includes determining a characteristic peak of the detected scattered laser beam light.

23. The method of claim 21, wherein determining a condition includes determining a type of machining mark.

24. A reconfigurable inspection apparatus for inspecting the surface finish of a plurality of machined surfaces in a part, the inspection apparatus comprising:
   a reconfigurable multi-spindle apparatus having a plurality of spindles;
   a plurality of inspection probes rotatably and movably supported on corresponding spindles, each inspection probe comprising:
      a laser that directs a laser beam perpendicularly to the machined surface;
      a detector positioned at an angle to the laser beam to detect scattered laser light from the surface; and
      a computer system including software that compares the detected scattered light to a scattered light signature from a first-type finishing mark and to a scattered light signature from a second-type finishing mark and determines a condition of the surface finish.

25. The inspection apparatus of claim 24, wherein the machined surfaces are cylinder bores and the part is an engine block.

26. The inspection apparatus of claim 25, wherein the distance between any two inspection probes is changeable without removing the corresponding spindles from the inspection apparatus.

27. An inspection probe for inspecting a surface finish of a manufactured surface, the probe comprising:
   a laser directing a laser beam perpendicularly to the manufactured surface;
   an optical detector positioned at an angle to the laser beam to detect scattered laser light from the surface;
   a computer system including software that compares the detected scattered light to a scattered light signature from a first-type finishing mark and to a scattered light signature from a second-type finishing mark and determines a condition of the surface finish, wherein the first and second finishing marks correspond to finishing marks before and after a removal of material.

28. An inspection probe for inspecting a surface finish of a manufactured surface, the probe comprising:
   a laser directing a laser beam perpendicularly to the manufactured surface;
   an optical detector positioned at an angle to the laser beam to detect scattered laser light from the surface;
   a computer system including software that compares the detected scattered light to a scattered light signature from a first-type finishing mark and to a scattered light signature from a second-type finishing mark and determines a condition of the surface finish, wherein the first and second finishing marks correspond to finishing marks before and after an addition of material.

* * * * *